United States Patent
Williams

(10) Patent No.: US 10,632,008 B2
(45) Date of Patent: Apr. 28, 2020

(54) GLANS PENIS EXTENDER OR FORESKIN RETRACTOR

(71) Applicant: Kent Williams, Purcellville, VA (US)

(72) Inventor: Kent Williams, Purcellville, VA (US)

( * ) Notice: Subject to any disclaimer, the term of this patent is extended or adjusted under 35 U.S.C. 154(b) by 235 days.

(21) Appl. No.: 15/834,382

(22) Filed: Dec. 7, 2017

(65) Prior Publication Data

US 2019/0175383 A1    Jun. 13, 2019

(51) Int. Cl.
*A61F 5/00* (2006.01)
*A61F 5/41* (2006.01)
*A61F 5/37* (2006.01)

(52) U.S. Cl.
CPC .................. *A61F 5/41* (2013.01); *A61F 5/37* (2013.01); *A61F 2005/411* (2013.01)

(58) Field of Classification Search
CPC ..... A61F 5/41; A61F 2005/411; A61B 17/326
USPC ...................................... 600/38–41
See application file for complete search history.

(56) References Cited

U.S. PATENT DOCUMENTS

| | | | |
|---|---|---|---|
| 1,608,806 A | 10/1925 | Nelson | |
| 3,799,157 A | 3/1974 | McIntire | |
| 3,893,455 A * | 7/1975 | McNally | A61B 17/326 600/41 |
| 4,440,183 A | 4/1984 | Miller | |
| 5,063,915 A * | 11/1991 | Wyckoff | A61F 5/41 128/842 |
| 5,713,830 A | 2/1998 | Tucker et al. | |
| 6,416,460 B1 | 7/2002 | Jochum | |
| 7,645,228 B2 | 1/2010 | Flores | |
| 7,802,577 B2 | 9/2010 | Cvetanovic | |
| 8,764,628 B2 | 7/2014 | Basden | |
| 2009/0113605 A1 | 5/2009 | Nicolosi et al. | |
| 2009/0318754 A1 | 12/2009 | Ettmer | |
| 2011/0146695 A1 | 6/2011 | Taouil | |
| 2012/0197074 A1 | 8/2012 | Basden | |
| 2012/0220820 A1 | 8/2012 | Gomez De Diego | |

FOREIGN PATENT DOCUMENTS

WO      2011/002203 A2    1/2011

* cited by examiner

*Primary Examiner* — John P Lacyk
(74) *Attorney, Agent, or Firm* — Jacobson Holman, PLLC.

(57) ABSTRACT

A device to keep a male glans penis exposed, by extending the glans penis or retracting the foreskin, consisting of a glans penis loop around the glans penis or foreskin and attached to a base strap extending along the underside of the scrotum and penis, which base strap is adjustable to extend the glans penis or retract the foreskin and thereby keeping the glans penis exposed.

8 Claims, 3 Drawing Sheets

GLANS PENIS EXTENDER OR FORESKIN RETRACTOR

BACKGROUND OF THE INVENTION

The invention relates to a male specific device which in particular relates to means that are meant to stretch or maintain the glans penis, thereby keeping the glans penis of the penis from retracting into the foreskin or body of the male. Alternately the foreskin is retracted from the glans penis.

There exists prior art for extending the penis, see U.S. Pat. Nos. 6,416,460 and 7,802,577. Other US patents for the purpose of maintaining an erection exists, see U.S. Pat. Nos. 5,713,830, 8,764,628 and US Patent 2012/0197074.

The anatomy of the penis which is the copulatory organ of the male of higher vertebrates in mammals also provides the channel by which urine leaves the body. The human penis is anatomically divided into two continuous areas, the body and the root and the penis is located directly below the area of the male torso between the legs. The root is long and cylindrical within the body and it expands into a mushroom-shaped structure called the glans penis. The body covers the root and terminates in a foreskin which covers the glans penis. This foreskin many times is fully or partially removed in a process called circumcision. Running through the center of the cylindrical root of the penis is the urethra, a common passage for semen and urine; the urethra ends in a slitlike opening at the tip of the glans penis.

SUMMARY OF THE INVENTION

It is now realized that when the male glans penis retracts or shrinks and the glans penis slips into the foreskin or the body of the male due to various factors such as temperature or age, it may cause some difficulty. Furthermore, the male may feel embarrassment or have anxiety when the retraction or shrinkage occurs in a public or private setting and the penis is intentionally or unintentionally viewed by another person.

When the male has to urinate, the retraction of the glans penis into the foreskin or body is especially problematic. The stream of urine can be deflected as it emerges from the glans penis often soiling the clothes of the male.

Therefore, what is needed is an extender attached to the glans penis keeping it from retracting or shrinking into the foreskin or body or foreskin retraction keeping the glans penis exposed. This problem has not been resolved or recognized in the prior art.

It is therefore the object of the present invention to provide a male genital organ extender, particularly of the glans penis or a foreskin retractor so as to keep the glans penis exposed. The glans penis is encircled by a piece of soft material which extends from the glans penis along the underside of the scrotum and penis and is incorporated with a strap or undergarment that wraps around the base of the penis and scrotum.

The extender or retractor may be made out of soft stretch or non-stretch material. A base strap wraps around the penis and scrotum and may be adjustable by the user or may be made of a continuous strap with the glans penis extender or foreskin retractor attached to the base strap on the underside of the male genitals. The extender or retractor may be used with the base strap and glans penis material loop only or with a fabric material that covers the extender as well as the penis and scrotum.

DESCRIPTION OF THE INVENTION

Figure 1:
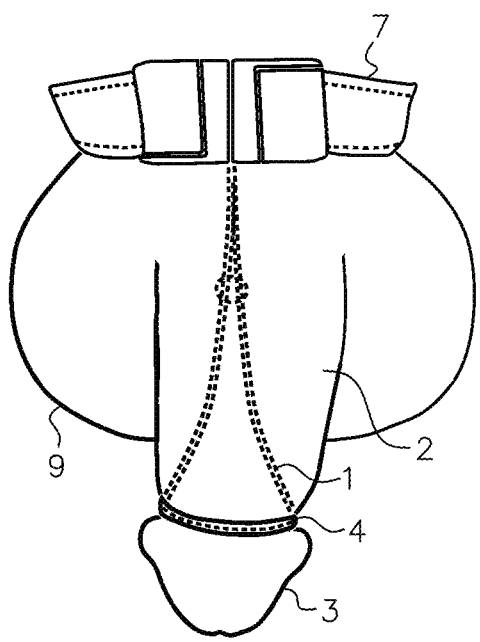
FIG. 1 is a top plan view of the present invention.
Figure 2:
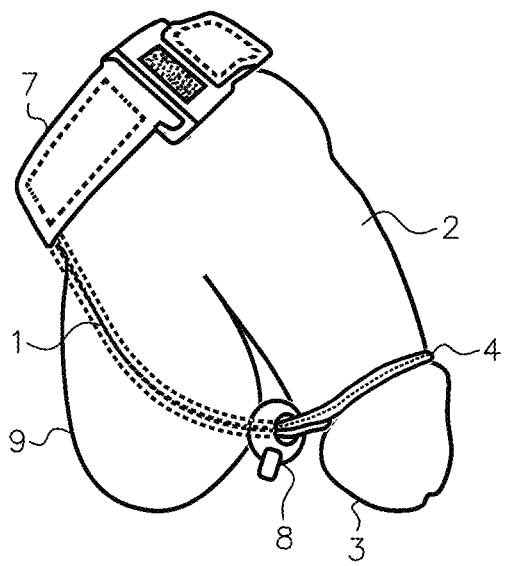
FIG. 2 is a left side view of FIG. 1.
Figure 3:
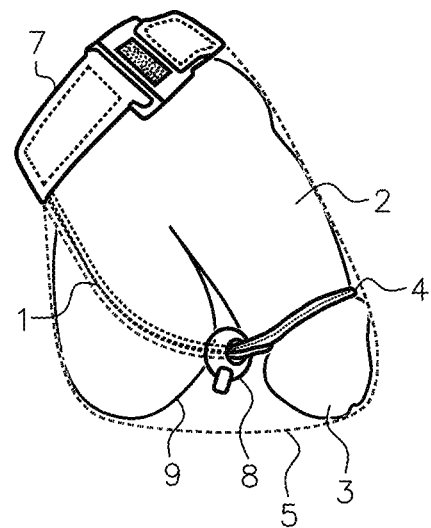
FIG. 3 is a left side view of FIG. 1 with a fabric cover.

The present invention provides a male genital organ extender or retractor to keep the glans penis exposed. When the male has to urinate, the retraction of the glans penis into the foreskin or body is especially problematic. A stream of urine can be deflected as it emerges from the glans penis thereby soiling the clothes. This may be true for circumcised or uncircumcised male genital organs.

The glans penis is extended or the foreskin is retracted by a base strap 1 which extends from the glans penis 3 along the underside of the scrotum 9 and the penis 2 and is incorporated with an encircling strap 7 which wraps around the penis 2 and the scrotum 9. Furthermore, there can be an undergarment 5 of fabric material which wraps around the penis 2 and the scrotum 9.

Figure 4:
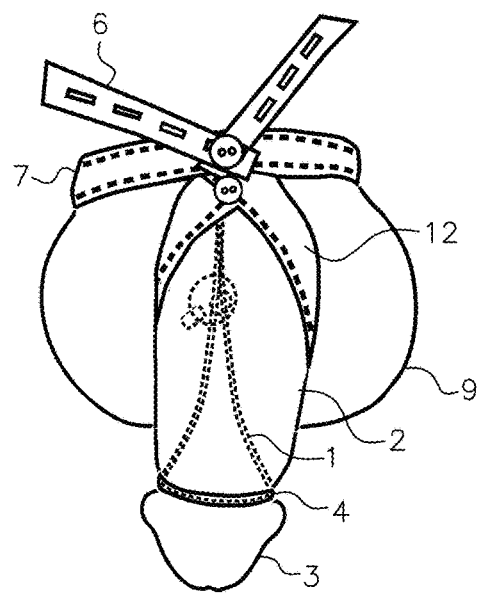
FIG. 4 is a top plan view showing an optional strap that wraps around the base of the penis, which strap is secured to an encircling strap that goes around the scrotum and penis and can further be attached to a waist strap.

The base strap 1 attached to the encircling strap 7 and which goes underneath the scrotum and goes around the glans penis, has an adjustable slide fastener 8 by which the user can adjust the extension of the glans penis or the retraction of the foreskin. The adjustable slide fastener has a spring biasing means to adjust the extension of the base strap and hence the extension of the glans penis or retraction of the foreskin to keep the glans penis exposed. Another embodiment, see FIG. 4, shows an optional strap 12 which wraps around the penis and is attached to the encircling strap 7 and further is attached to a waist strap 6 which goes around the waist of the user.

The base strap 1 which has a glans penis loop 4 and goes underneath the scrotum up to the glans penis, can be placed around the penis just behind the glans penis 3 on the foreskin as an alternative position to prevent the glans penis 3 from retracting into the foreskin or body by retracting the foreskin. See FIG. 5. The base strap is connected to an alternate strap 13 which goes under the scrotum and keeps the foreskin of the penis from covering the glans penis.

Figure 5:
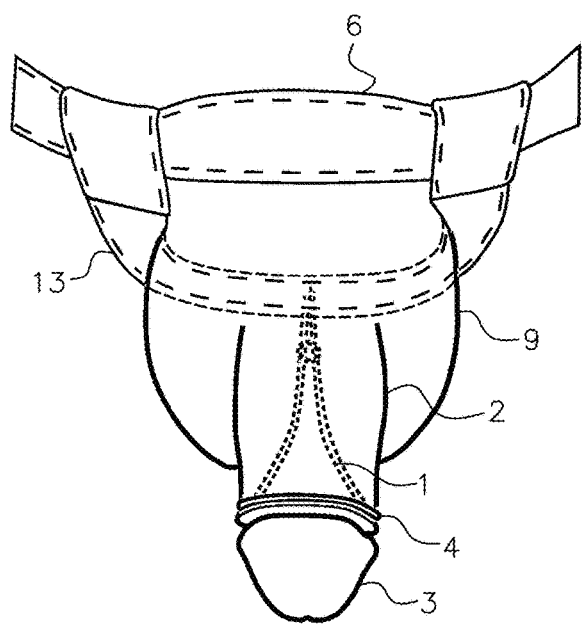
FIG. 5 is a top plan view of an alternative embodiment that shows a waist strap with an attached strap running under the scrotum and penis;
the base strap that keeps the foreskin retracted from the glans penis is attached to this strap and the base strap in this embodiment secures the foreskin of the penis just behind the glans penis to keep the glans penis from retracting into the foreskin or body by retracting the foreskin from the glans penis.
Figure 6:
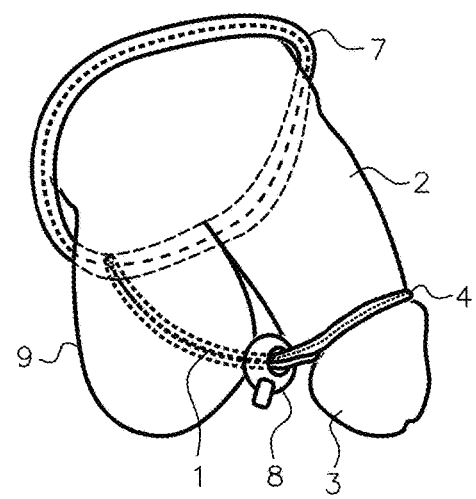
FIG. 6 is a left side view of FIG. 1 showing the placement of an adjustable slide fastener.
Figure 7:
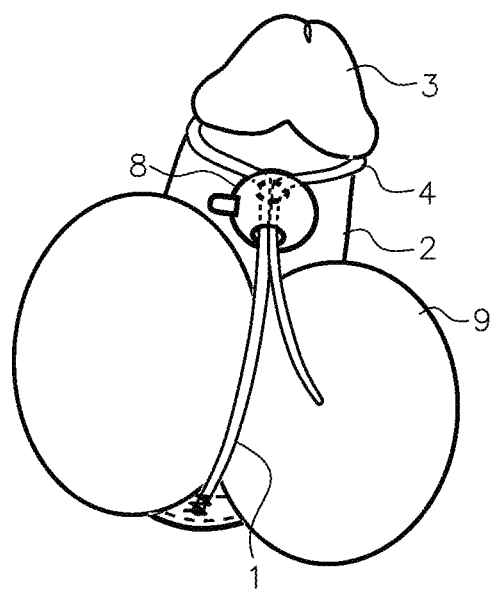
FIG. 7 is a bottom view of FIG. 1 showing the placement of an adjustable slide fastener.

The base strap 1 which goes underneath the scrotum and attaches to the glans penis loop 4 has an adjustable slide fastener 8 whereby the tension on the foreskin in FIG. 5 retracts the foreskin from the glans penis.

Figure 8:
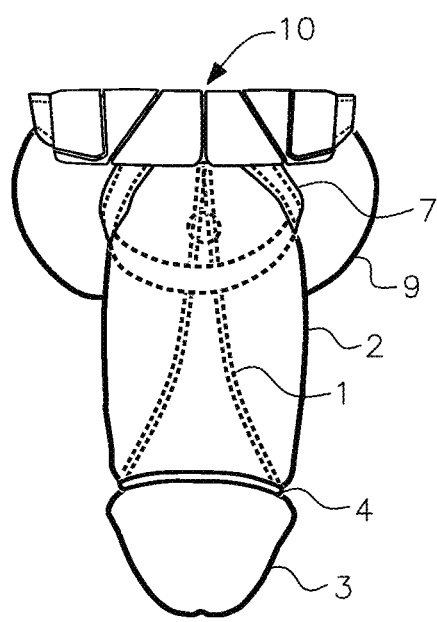
FIG. 8 is a top view of FIG. 1 showing a buckle that takes the ends of the encircling strap which the user will adjust to the length that best fits.
Figure 9:
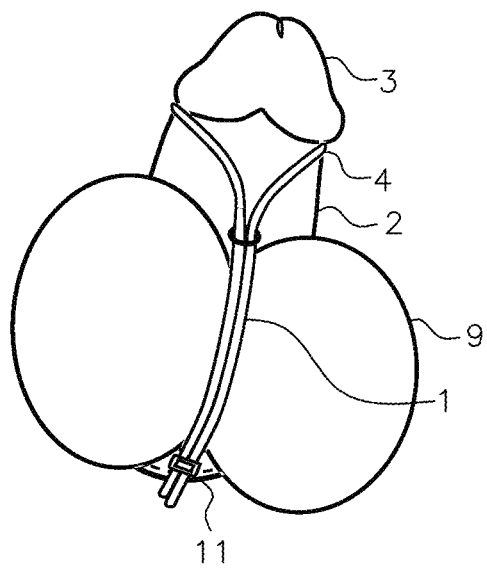
FIG. 9 is a bottom view of FIG. 1 showing the placement of an adjustable glans penis fastener that is on the base strap that goes under the scrotum and glans penis, the adjustable glans penis fastener can be adjusted by the user to the length he desires.

FIG. 8 shows the base strap 1 attached to the glans penis loop 4 along with the encircling strap 7, all of which are attached to a buckle 10. The ends of the encircling strap 7 are placed into the buckle 10 to adjust the fit. FIG. 9 shows the base strap 1 underneath the scrotum 9 and encircling the penis with the glans penis loop 4 at the glans penis 3, which base strap has an adjustable glans penis fastener 11. This fastener can adjust the base strap such as to adjust the downward force on the glans penis to prevent it from retracting into the foreskin or body.

The invention claimed is:

1. A device to keep a glans penis exposed by extending the glans penis or retracting a foreskin comprising a fabric base strap which encircles the glans penis with a glans penis loop and passes under the scrotum and attaches to a fabric material encircling strap which encircles the penis and scrotum of a male body adapted to wear the device;

and an adjustable slide fastener on the base strap to be adjusted to tighten the glans penis loop around the glans penis or the foreskin to permit the glans penis to be extended or the foreskin to be retracted thereby keeping the glans penis exposed.

2. The device as claimed in claim 1, wherein there is fabric material encircling the penis and the scrotum.

3. The device as claimed in claim 1, wherein the encircling strap around the penis and the scrotum is adjustably attached to a waist strap.

4. The device as claimed in claim 1, wherein the base strap consists of at least one line attached to the encircling strap which is around the penis and the scrotum and passing through the adjustable slide fastener.

5. The device as claimed in claim 1, wherein the adjustable slide fastener has an aperture through which lines of the base strap pass and an adjustable glans penis fastener for securing the lines after being adjusted to the desired extension of the glans penis to prevent it from retracting into the foreskin.

6. The device as claimed in claim 3, wherein the waist strap is adjustable.

7. The device as claimed in claim 4, wherein the adjustable slide fastener on the base strap which is attached to the encircling strap which ends are placed in a buckle which can be adjusted thereby extending the glans penis or retracting the foreskin, wherein a waist strap is used to adjust the tension of the encircling strap on the penis.

8. The device as claimed in claim 1, wherein the glans penis loop is placed slightly behind the glans penis on the foreskin to retract the foreskin thereby keeping the glans penis exposed.

* * * * *